(12) United States Patent
Lumsden et al.

(10) Patent No.: US 9,131,311 B2
(45) Date of Patent: Sep. 8, 2015

(54) CANAL PHONES WITH STRUCTURE AND METHOD FOR SELECTIVELY PASSING OR BLOCKING ENVIRONMENTAL AMBIENT SOUND AND SWITCHABLE ELECTRICAL CONNECTIONS

(75) Inventors: Stuart W. Lumsden, Baltimore, MD (US); Ken Chae, Baltimore, MD (US); Scott Orth, Baltimore, MD (US); David Fitzpatrick, Baltimore, MD (US)

(73) Assignee: Polk Audio, LLC, Baltimore, MD (US)

( * ) Notice: Subject to any disclaimer, the term of this patent is extended or adjusted under 35 U.S.C. 154(b) by 1004 days.

(21) Appl. No.: 13/253,768

(22) Filed: Oct. 5, 2011

(65) Prior Publication Data

US 2012/0087511 A1    Apr. 12, 2012

Related U.S. Application Data

(60) Provisional application No. 61/390,998, filed on Oct. 7, 2010, provisional application No. 61/474,610, filed on Apr. 12, 2011.

(51) Int. Cl.
*H04R 1/10* (2006.01)
*A61F 11/08* (2006.01)

(52) U.S. Cl.
CPC .............. *H04R 1/1091* (2013.01); *A61F 11/08* (2013.01); *H04R 1/1016* (2013.01); *H04R 1/1083* (2013.01); *H04R 1/1041* (2013.01)

(58) Field of Classification Search
CPC .. H04R 1/1016; H04R 1/1041; H04R 1/1083; H04S 1/005; A61F 11/06; A61F 11/08
USPC .................................... 381/74, 351, 372, 373
See application file for complete search history.

(56) References Cited

U.S. PATENT DOCUMENTS

| 8,385,560 B2* | 2/2013 | Solbeck et al. .............. 381/71.8 |
| 2010/0061582 A1* | 3/2010 | Takigawa et al. ............. 381/380 |
| 2010/0166245 A1* | 7/2010 | Takigawa et al. ............. 381/380 |
| 2012/0207320 A1* | 8/2012 | Avital ............................. 381/74 |

* cited by examiner

*Primary Examiner* — Davetta W Goins
*Assistant Examiner* — Daniel Sellers
(74) *Attorney, Agent, or Firm* — McKinney & Associates, LLC; J. Andrew McKinney, Jr.

(57) ABSTRACT

A canal phone incorporates a transducer within an isolation sound chamber for reproducing sound from an audio source, and a sound-transmission passageway, or ambient sound port, for allowing ambient sounds to enter the isolation sound chamber. The passageway has inner and outer apertures, one oriented towards the ambient noise environment outside of the listener's ear and the other oriented toward the isolated chamber formed by the space between a loudspeaker diaphragm within the canal phone and the tympanum of the listener's ear. The canal phone has a port blocking switch mechanism that selectively opens or closes the aperture of the passageway that is open to the ambient noise. This switch mechanism may also electrically disconnect the transducer and seal either the outer or the inner end of the passageway in different embodiments of the invention.

21 Claims, 8 Drawing Sheets

CANAL PHONES WITH STRUCTURE AND METHOD FOR SELECTIVELY PASSING OR BLOCKING ENVIRONMENTAL AMBIENT SOUND AND SWITCHABLE ELECTRICAL CONNECTIONS

RELATED APPLICATION INFORMATION

This application claims the benefit of, commonly owned U.S. Provisional Patent Application No. 61/390,998, filed 7 Oct. 2010, and entitled "Canalphones With Structure and Method for Selectively Passing or Blocking Environmental Ambient Sound", and also claims the benefit of, commonly owned U.S. Provisional Patent Application No. 61/474,610, filed 12 Apr. 2011, and entitled "Canalphones With Structure and Method for Selectively Passing or Blocking Environmental Ambient Sound and Switchable Electrical Connections," the entire disclosures of which are hereby incorporated herein by reference.

BACKGROUND OF THE INVENTION

1. Field of the Invention

The present invention relates, in general, to methods and structures for reproduction of sound, and more specifically to the application of acoustic and psychoacoustic principles in the design of an in-ear headphone or in-ear loudspeaker system and to structures incorporating such design principles.

2. Discussion of the Prior Art

One of the most convenient and popular speaker solutions for portable personal audio is the use of in-ear headphones. These headphones can provide exceptional sonic performance and since they can be made to be both light and secure in the listener's ears, provide great convenience, especially for a physically active listener. One type of in-ear headphone, sometimes called "canal phones", is meant to be placed into the listener's ear canal. They have soft tips surrounding a sound emitting aperture which is oriented in the ear canal towards the tympanum, and are intended to provide a comfortable yet complete acoustic seal between the sound emitting aperture and the outside environment (as illustrated in FIGS. 1-6). This arrangement enhances the perceived acoustic performance of the canal phones and provides exceptional acoustic isolation from the surrounding environment, which is desirable for listening.

One difficulty encountered with such prior art canal phones is that isolation from the surrounding environment is not helpful in many situations, because the listener may have to remove at least one canal phone in order to hear ambient sounds or to communicate with others. Furthermore, positioning the canal phones properly in a listener's ears requires care in order to achieve both comfort and a good acoustic seal for maximum listening performance. Improper positioning of a canal phone can cause ear fatigue or even pain when worn for several minutes or more. Typically, manufacturers provide multiple types and sizes of soft canal phone tips so the listener can select a specific soft tip to find the best fit. The listener or user will typically need to spend some time trying to fit a canal phone comfortably within his or her ear canal, and the insertion and fitting process for finding the best comfort, acoustic isolation and sound quality often requires pushing on the canal phone, pulling or tugging on the ear and removing and re-inserting the canal phone. Then, once the listener has obtained a satisfactory fit for the canal phone, he or she does not want to remove it and then have to go through the insertion and fitting process again, but the user may need to hear something or someone. As a result, the acoustic isolation from a properly fitted canal phone frustrates a listener who may momentarily want to hear something or someone.

Others have developed audiologist's products (such as hearing aids) which permit an "ear-plug" structure to be adapted in a manner which allows some sound from the environment to pass into the ear canal. Musicians who perform music styles noted for their loud nature, especially rock music, often wear earplugs to prevent their own performances from damaging their hearing. Musicians' earplugs are designed to attenuate sounds evenly across the audio band and thus minimize their effect on the user's perception of bass and treble levels. These are commonly used by musicians and technicians, both in the studio and in concert, to avoid overexposure to high sound pressure or volume levels. Musicians' earplugs typically include a central tubular body with an open interior lumen, a proximal end adapted to fit within the ear canal and a distal end which projects outwardly to give the user something to grasp and manipulate. The distal end of the tubular body can be open to the environment or closed and can define an acoustic transmission line with a damper or attenuator at the closed distal end. The tubular body's proximal end carries one or more compliant, rubbery domed flanges shaped to form a seal in outer part of the ear canal. The proximal end of the tubular body defines a sound output port or small hole at the proximal end of the plug, so attenuated sound can pass into the ear canal. However, such earplugs are not suitable for listening to high quality recorded sound unimpeded by ambient noise.

Other devices which permit a user to hear at least some ambient sound include safety equipment which incorporates active electronics either to cancel environmental sounds or to allow the listener to hear them, but such devices require the use of microphones, amplification, noise filtering/canceling circuits and power that must be provided either from the source electronics or batteries. These requirements create additional cost, bulk and inconvenience.

Figure 3A:
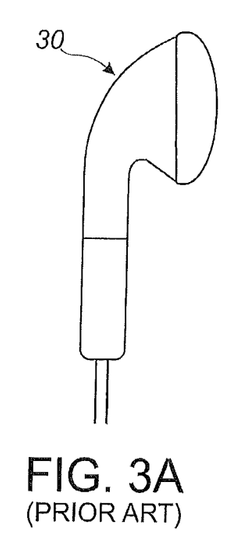
FIG. 3A is a side view of a typical "ear bud" type audio earpiece.
Figure 5:
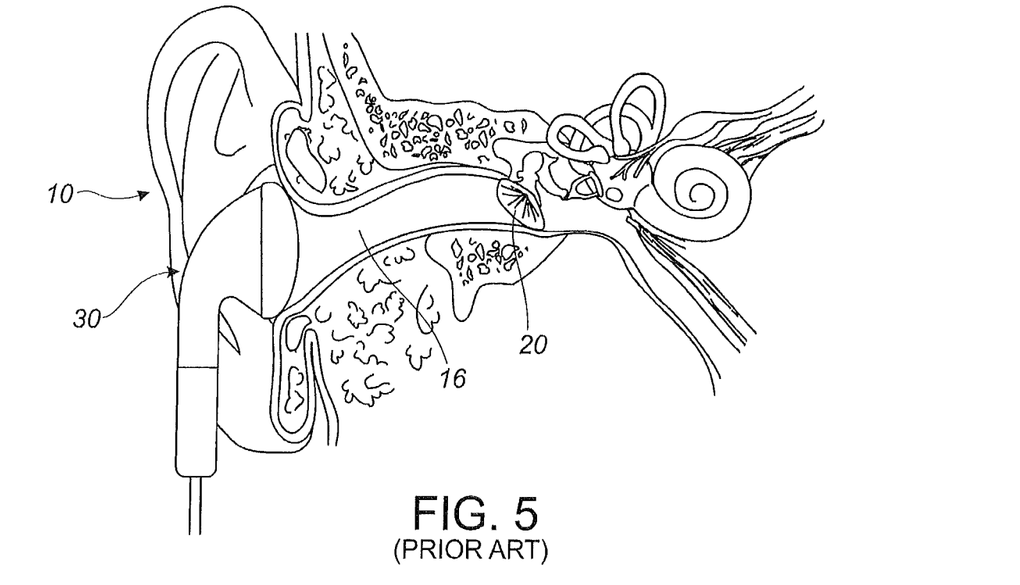
FIG. 5 illustrates the ear bud of FIG. 3A positioned normally in the human ear of FIG. 2, the ear bud being positioned in the concha, between the tragus and anti-tragus.
Figure 6:
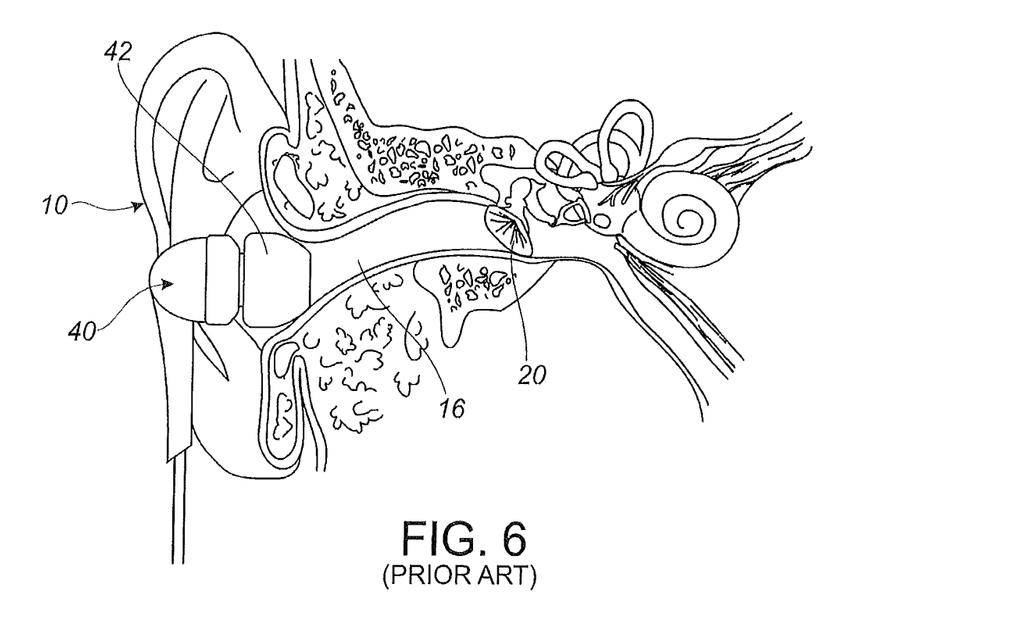
FIG. 6 illustrates the canal phone of FIG. 3B positioned normally in the ear canal of the human ear of FIG. 2.

Headphones known as ear-buds are also available (see, e.g., FIG. 3a and FIG. 5). These sit in the lower pinna portion of the ear, and are typically fitted to the listener by having the larger portion of the ear-bud in the listener's lower concha, sometimes called the cava, between the tragus and anti-tragus portions of the ear. But ear-buds typically do not fit snugly in the ear canal when positioned according to the manufacturer's instructions, and do not create an acoustic seal. Therefore, they do not create much acoustic isolation and always allow passage of a significant amount of environmental sound.

There are also headphones known as supra-aural headphones. These typically allow the passage of more environmental sound to the listener via leakage because they do not produce a particularly good seal to the listener's ear. Unfortunately, this also often results in poorer acoustic performance of the headphones and, since the leakage cannot be switched off, the listener typically cannot eliminate this distraction at appropriate times nor achieve optimum acoustic headphone performance.

There is a need, therefore, for a convenient, flexible, inexpensive and unobtrusive earphone structure and method for selectively passing or blocking environmental ambient sound, while permitting the user to enjoy high fidelity or "audiophile" quality sound playback.

OBJECTS AND SUMMARY OF THE INVENTION

Accordingly, it is an object of the present invention to overcome the above mentioned difficulties by providing a method for easily modifying a canal phone's acoustic properties in order to produce a structure that will enable a user to maximize or minimize acoustic isolation and audio playback to suit the situation at hand, while the canal phone remains properly positioned in the listener's ear.

Briefly, in a preferred embodiment of the present invention, a canal phone is designed to incorporate a selectively isolated sound chamber for use, for example, in reproducing sound from an audio source, and an ambient sound-transmission passageway or sound port, for allowing environmental or ambient sounds to enter the isolated sound chamber. The ambient sound passageway, which may have a cross sectional area that is equivalent to or greater than that of a 2 mm diameter tube, has inner and outer apertures, one oriented towards the ambient noise environment outside of the listener's ear and the other oriented toward the isolation chamber formed by the space between a loudspeaker diaphragm within the canal phone and the tympanum of the listener's ear. The canal phone of the present invention has a two-state user controllable stopper switch mechanism that is capable of sealing the aperture of the passageway that is open to the ambient noise. This stopper is connected to a mechanical linkage which allows the stopper to be moved either into or out of a sealing position at the outer aperture and to stay securely in either position once moved there by the user or wearer. This stopper mechanism may seal either the outer or the inner end of the passageway, in different embodiments of the invention. The two-state user controllable stopper switch mechanism includes a mechanical linkage may be in various forms, such as a rocker, a slide, or a rotating cover, for example, as long as it not only selectively opens or covers the passage but when the opening is covered it effectively seals the opening acoustically.

More particularly, it will be appreciated by persons having skill in the art that the canal phone assembly of the present invention basically comprises an elongated, hollow or tubular housing or body having an outer end wall and an inner open end disposed opposite the end wall. The hollow body portion has a rear or outer enclosure with a volume configured to receive and support a transducer, or dynamic driver and also defines an inner or front sound chamber terminating in the inner open end, so that sound generated by the transducer propagates into and through the front sound chamber and out through the inner open end. A cable including a plurality of (e.g., two) electrical conductors or wires extends from an electrical audio signal source external to the housing, the cable being secured to the outer end wall of the housing and electrically connected to the transducer for converting electrical energy received via the plurality of electrical conductors to sound energy which is directed into the front sound chamber.

The housing also defines a hollow elongated passageway or lumen having an open end inner end terminating in the front sound chamber and an open outer end terminating at an outer aperture defined in the outer or distal end wall. The outer end wall carries a selectively actuable stopper switch mechanism, or sealing member, configured to permit a user either (a) to plug, block, occlude or cover and seal off the outer aperture defined in the outer end wall, or (b) to uncover the outer aperture defined in the outer end wall so that sound from the ambient environment can pass into and through the outer aperture defined in the outer end wall and propagate into the front sound chamber, to co-mingle with sound generated by the transducer.

An ear tip or sealing member is formed from a resilient material and is removably disposed over the housing's proximal end for sealing with an ear canal of a user. In this way, the canal phone is configured to be easily inserted into and to substantially acoustically seal the ear canal of the wearer when inserted. Preferably, a plurality of interchangeable ear tips of varying shapes is provided with the canal phone assembly as part of a kit so that the user can select a desired ear tip shape.

Typically, the acoustic isolation afforded by canal phones is on the order of −20 dB or more and is broadband in frequency, from about 50 Hz to well beyond 20 kHz, and this isolation is similar to some types of sound isolation earplugs. The improved canal phone of the present invention incorporates the stopper switch mechanism discussed above for opening or closing a through passageway having an aperture, or port, facing that portion of the ear canal that is between the canal phone transducer diaphragm and the tympanum in the listener's ear. The port preferably has a surface area of only a few square millimeters, and allows the passageway through the canal phone to be opened to allow much of the ambient sound to reach the tympanum and to be heard at a reasonably normal level, up to a cut-off point in frequency that is dictated by the characteristics of the passageway, which acts as a low-pass filter. In the present invention, this port or passageway structure is acoustically tuned (e.g., by the choice of aperture, length and resistive acoustic loading) to allow the listener to open the passageway to hear the ambient audio within a band-limited frequency range; e.g., 50-1 kHz, at normal levels and to hear the frequency band 1 kHz-3 kHz, or possibly higher, at levels that are reduced by only 10-15 dB from normal. The port or passageway is thus configured as an acoustical transmission structure tuned to enhance the intelligibility of speech and other important ambient sounds.

As an even greater convenience, miniature electrical contacts can be placed within the mechanical linkage of the switch mechanism that is used for opening and closing the passageway, so that an electrical connection to the speaker transducer within the canal phone can disconnected by the switch when the passageway is opened to ambient sound so that the sound produced by the transducer does not interfere with ambient sound entering through the passageway when a user or wearer wishes to concentrate on listening to ambient sounds from the surrounding environment.

BRIEF DESCRIPTION OF THE FIGURES

The foregoing, and still further objects, features and advantages of the present invention will become apparent upon consideration of the following detailed description of a specific embodiment thereof, particularly when taken in conjunction with the accompanying drawings, wherein like reference numerals in the various figures are utilized to designate like components, and wherein.

DESCRIPTION OF PREFERRED EMBODIMENTS

Figure 1:
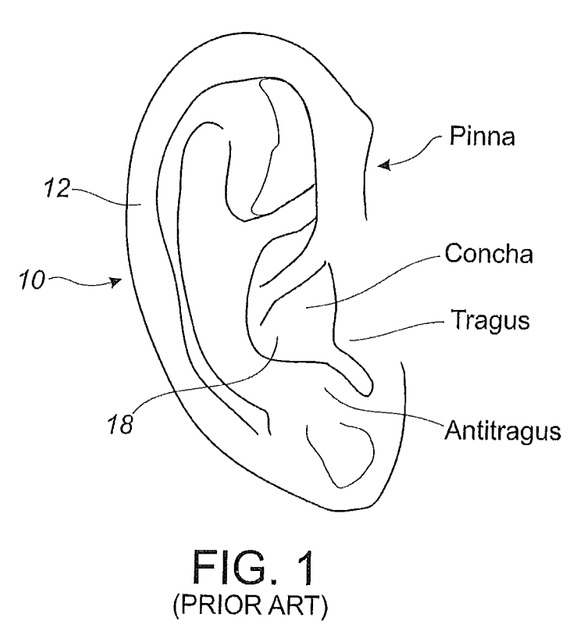
FIG. 1 illustrates the anatomy of the exterior portion of a human ear.
Figure 2:
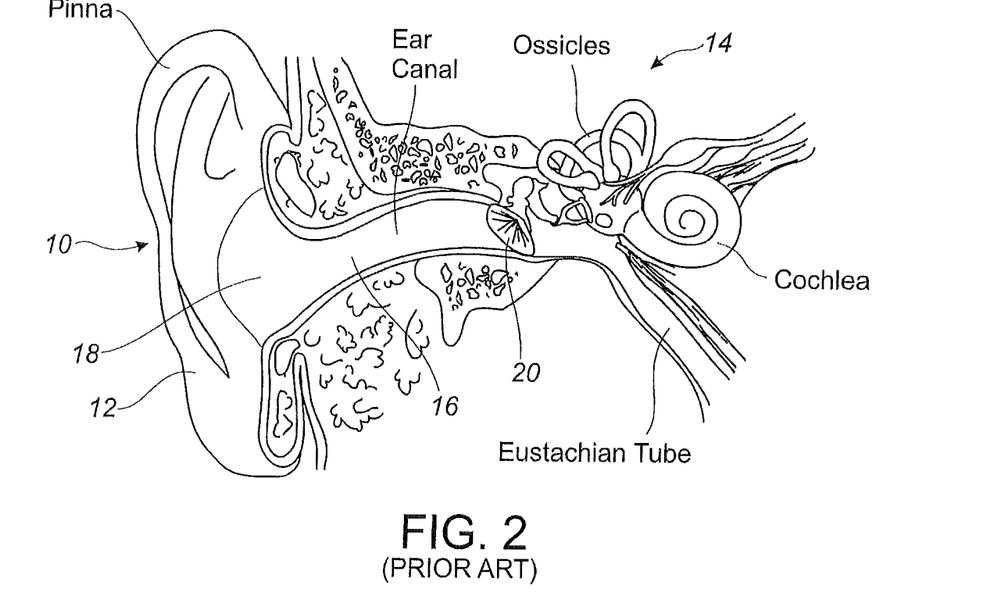
FIG. 2 is a cross-sectional view of the human ear, illustrating the parts of the middle and inner ear.

Referring now to the drawing FIGS. 1-15, FIGS. 1 and 2 illustrate, for purposes of convenient reference, a human ear 10, FIG. 1 showing its external portions 12 and FIG. 2 showing, in cross-section, its inner portions generally indicated at 14. The inner ear includes, for purposes of this description, an ear canal 16 leading from the concha 18 of the external ear to the ear drum 20.

Figure 3B:
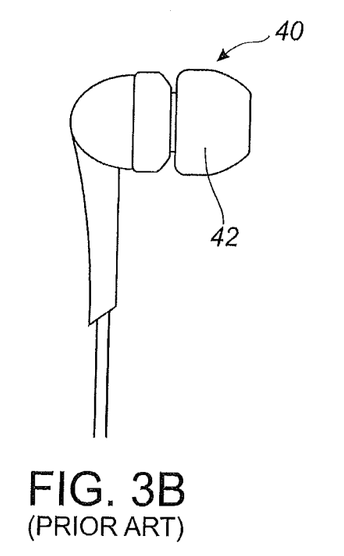
FIG. 3B is a side view of a typical "canal phone" type of audio earpiece.
Figure 4:
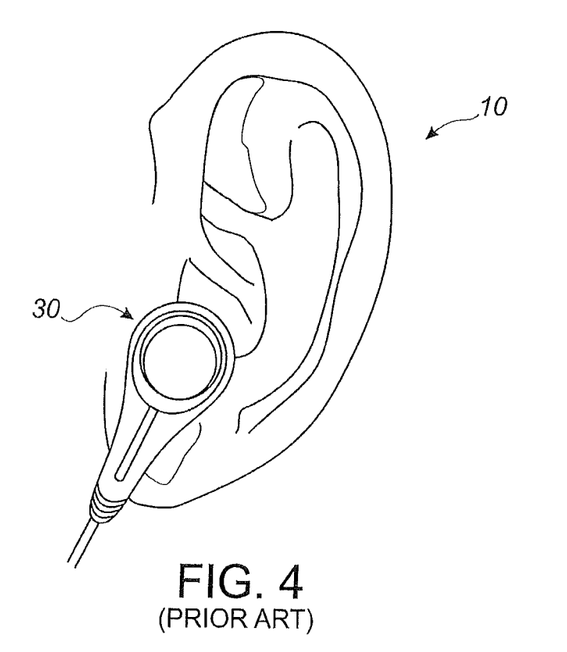
FIG. 4 is an external view of an ear bud positioned normally in a human ear.

As discussed above, two types of ear-inserted audio devices are in general use for providing audio signals to a listener in a convenient way, a conventional ear bud 30 as illustrated diagrammatically in FIG. 3A and a conventional canal phone 40, as illustrated diagrammatically in FIG. 3B. Both of these devices are designed to fit in the ear canal of a listener's ear, as illustrated in FIGS. 4 and 5 by the ear bud 30 positioned in the ear 10, and in FIG. 6 by the canal phone 40 positioned in ear 10. As known, such ear buds and canal phones transmit sound from a suitable source to the listener's ear to provide a personal audio source that serves to produce sound that generally is not interrupted by outside, or ambient, noise. As illustrated, the ear bud 30 generally is secured in the concha, whereas the canal phone 40 incorporates a soft tip 42 at its inner end which extends into the ear canal to produce a more secure fit that tends to better exclude ambient noise, so that the listener is isolated from outside sounds. As discussed above, such isolation can have advantages for obtaining high quality sound reproduction from, for example, a recorded source, but can have undesirable consequences when the listener wishes to hear ambient sounds.

Figure 7A:
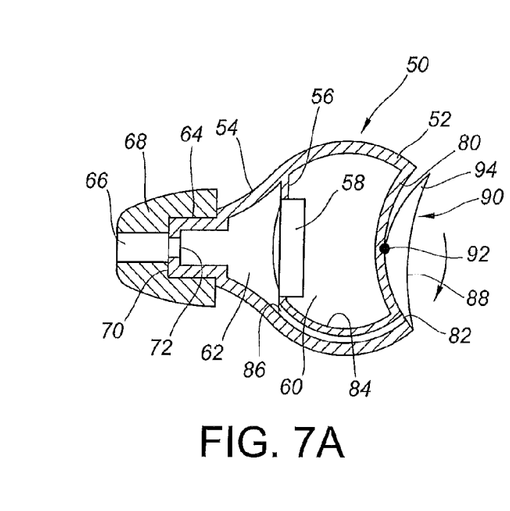
FIGS. 7A and 7B are diagrammatic cross-sectional illustrations of a first embodiment of the improved canal phone of the present invention, showing the open and closed positions of a hinge mechanism for admitting and excluding ambient noise, in accordance with the present invention.
Figure 7B:
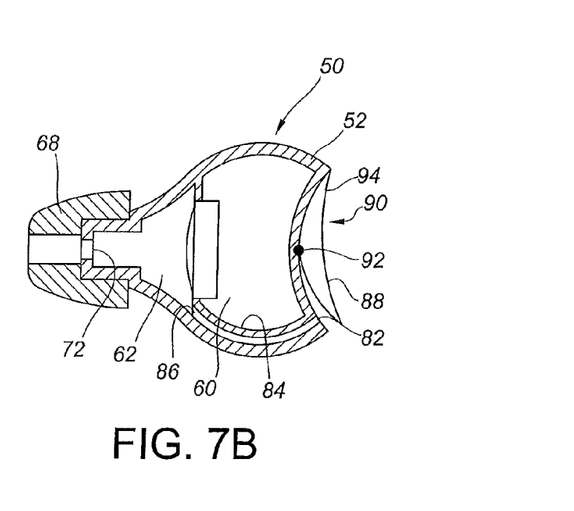

In accordance with the structure and method of the present invention, a canal phone assembly 50 suitable for use by an audiophile, or any listener, is illustrated in FIGS. 7A and 7B, to which reference is now made. This illustration is diagrammatic, for purposes of illustrating the concept of the invention, and although a preferred application in an audio system is described, it will be understood that a number of the described and illustrated features of the invention are not limited to any particular use. Certain of these features may be used, for example, in the construction of headphones or hearing aids.

The illustrated canal phone assembly 50 comprises a rearward, or outer housing portion 52 and a front, or inner housing portion 54 and preferably is generally cylindrical with an inner divider wall 56 supporting a transducer 58 dividing the inner and outer housing portions. The outer portion of the housing forms an outer chamber 60, while the inner portion of the housing forms an inner chamber 62, with the two chambers being separated by the transducer 58 and the wall 56. The front housing portion 54 has a tubular extension 64 which projects inwardly and which defines an extension of the inner sound chamber 62. This extension portion is inserted into a central opening 66 in a soft tip 68, which is configured and selected to be inserted into the entrance of an ear canal of the user and which serves as an acoustic coupling device to help isolate the inner ear from external ambient sound. The inner sound chamber 62 has a forward, or inmost end wall 70 which incorporates an output port 72 that is aligned with the central aperture 66 in the soft tip. The transducer 58 preferably has electrical input terminals (not shown) and is operative for generating an acoustic output signal at the output port 72 as a function of an electrical signal applied to its terminals.

The outer, or rear housing portion 52 has a rearmost end wall 80, through which extends an ambient sound port 82 that is connected by way of a passageway, or tube 84 through chamber 60 to an opening 86 in the divider wall 56 into the inner sound chamber 62. The port 82 is closable by one end 88 of an ambient sound switch or two-state user controllable stopper switch mechanism 90 which, in this embodiment, is a pivoted button, or cover that is mounted on a hinge mechanism 92. The cover can be pivoted about hinge 92 by the user pressing either the lower end 88 or an upper end 94 of the cover. Thus, as viewed in FIGS. 7A and 7B, the cover 90 can be pivoted downwardly (FIG. 7A) to a closed position by pressing end 88 to cause that end of the cover to engage port 82, thereby closing the passageway 84 to prevent ambient sound from entering the sound chamber 62, and can be pivoted upwardly to an open position by pressing end 94 to open the port 82 and to admit ambient sound to chamber 62. Accordingly, the inner ear of the user of the canal phone 50 can be isolated from ambient external sounds by closing the cover 90, or can be exposed to ambient external sounds by opening the cover.

Two-state user controllable stopper switch mechanism or sound switch 90 thus allows a user to select between (a) a first, sealed state where ambient sound passageway 84 is closed, thus acoustically isolating the listener for enhanced listening performance and (b) a second, open state wherein ambient sound passageway 84 is in open fluid communication with the outside atmosphere and the user can more easily perceive ambient sounds from his or her surrounding environment.

Figure 8A:
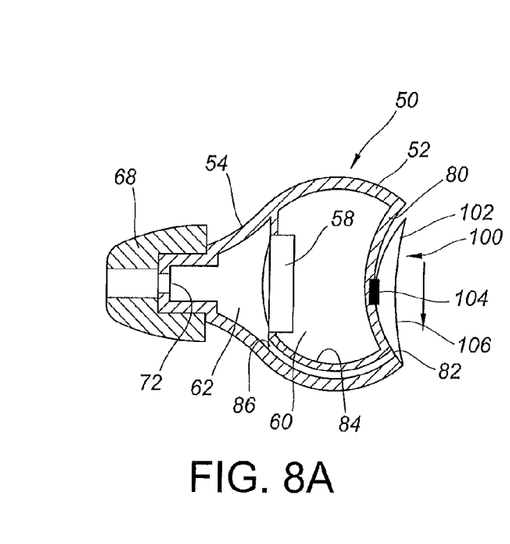
FIGS. 8A and 8B are diagrammatic cross-sectional illustrations of a second embodiment of the improved canal phone of the present invention, showing the open and closed positions of a slide mechanism for admitting and excluding ambient noise, in accordance with the present invention.
Figure 8B:
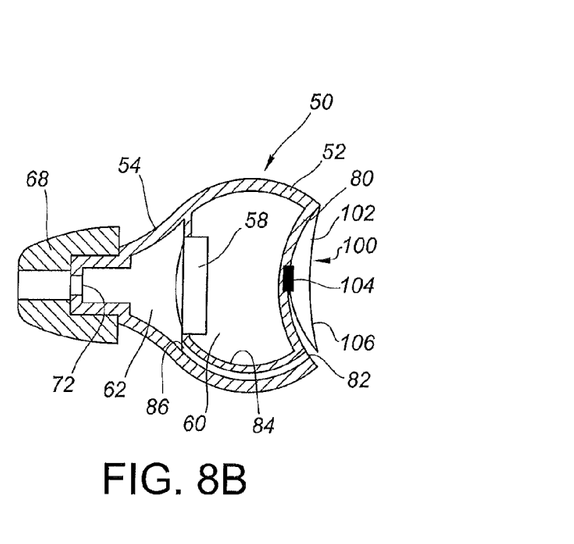

A modification of the ambient sound switch 90 is illustrated in FIGS. 8A and 8B, wherein elements in common with the embodiment of FIGS. 7A and 7B are similarly numbered. In this embodiment, an ambient sound switch 100 is in the form of a sound-blocking slider 102 mounted on the rear wall 80 of the canal phone 50 by a slide mechanism 104 for up and down motion along the face of wall 80. The hinge mechanism may be in the form of a T-shaped block mounted for sliding motion in a corresponding T-slot in the face of the wall so that the user may move the slider 102 downwardly to cause the lower end 106 of the slider to engage and cover the ambient sound port 82, as illustrated in FIG. 8A. The user may open the sound port to allow ambient sound to enter the sound chamber 62 by way of port 82 and passageway 84 by moving slider 102 upwardly, to expose port 82 as illustrated in FIG. 8B. Two-state user controllable stopper switch mechanism or sound switch 100 thus allows a user to select between (a) a first, sealed state where ambient sound passageway 84 is closed, thus acoustically isolating the listener for enhanced listening performance and (b) a second, open state wherein ambient sound passageway 84 is in open fluid communication with the outside atmosphere and the user can more easily perceive ambient sounds from his or her surrounding environment.

It will be understood that the foregoing two embodiments are illustrative of the invention, and that other switchable mechanisms may be used to act as a removable cover, or stopper, for the sound port 82 and, further, that although blockage of the passageway 84 at port 82 is convenient, the passageway can be selectively blocked and acoustically sealed at any point along its length to serve the same purpose of selectively blocking or admitting ambient external sound to the inner chamber 62 of the canal phone.

As illustrated in each of FIGS. 7A, 7B, 8A and 8B, the acoustic coupling device 68 may be in the form of a soft tip, or ear tip of a soft compliant material secured at the innermost end portion 64 to conform to the inner surface portions of the entrance of the ear canal of the user. The assembly 50 may also include at least one inner portion, as at 54, that is of generally conical form and of progressively inwardly decreasing diameter, arranged to engage the inner surface of the user's ear canal. This construction provides a seal that limits transmission of ambient sound to the ear canal around the outside of the canal phone, so as to provide isolation and a high quality sound reproduction chamber inside the canal phone. As discussed above, this sound isolation, although desirable for high quality sound during audio signal playback, effectively seals out and attenuates all ambient sounds and not only makes communication between the listener and others difficult, but can have undesired consequences. The movable sound switches exemplified by the embodiments discussed above and illustrated in FIGS. 7A-8B allow selective opening of the canal phone to the transmission of ambient sounds through the canal phone by way of passageway 84 to break the audio isolation and to provide a lumen for spoken or audible communication even when the canal phone is fully inserted and in use.

It will be understood that an exemplary canal phone in accordance with the present invention includes a pair of the canal phone assemblies 50 for insertion into the entrances of the left and right ear canals of a user. Optionally, a pair of input cables connect the left and right canal phones to a junction unit and a common cable connects the junction unit to a plug connector which may be connected to an output jack of an audio signal source or listening device, such as a portable media player. The construction of the left and right canal phones is preferably substantially identical, with each incorporating a transducer 58 which is mounted between the front and rear portions 52 and 54 of the assembly 50, with the transducer facing into the rear enclosure or chamber 62 of the housing.

As is known in the construction of canal phones, the transducer 58 preferably has electrical input terminals (not shown) and is operative in response to electrical signals supplied to the terminals to generate an acoustic output signal at the inner port 72 for transmission into the ear of the listener. The terminals of the left and right canal phone transducers are connected through wires to conductors in their respective input cables, and an outer sheath of the cable is preferably bonded to a strain relief member. This strain relief member is preferably secured in an opening in the end wall or end cap 80.

Figure 9:
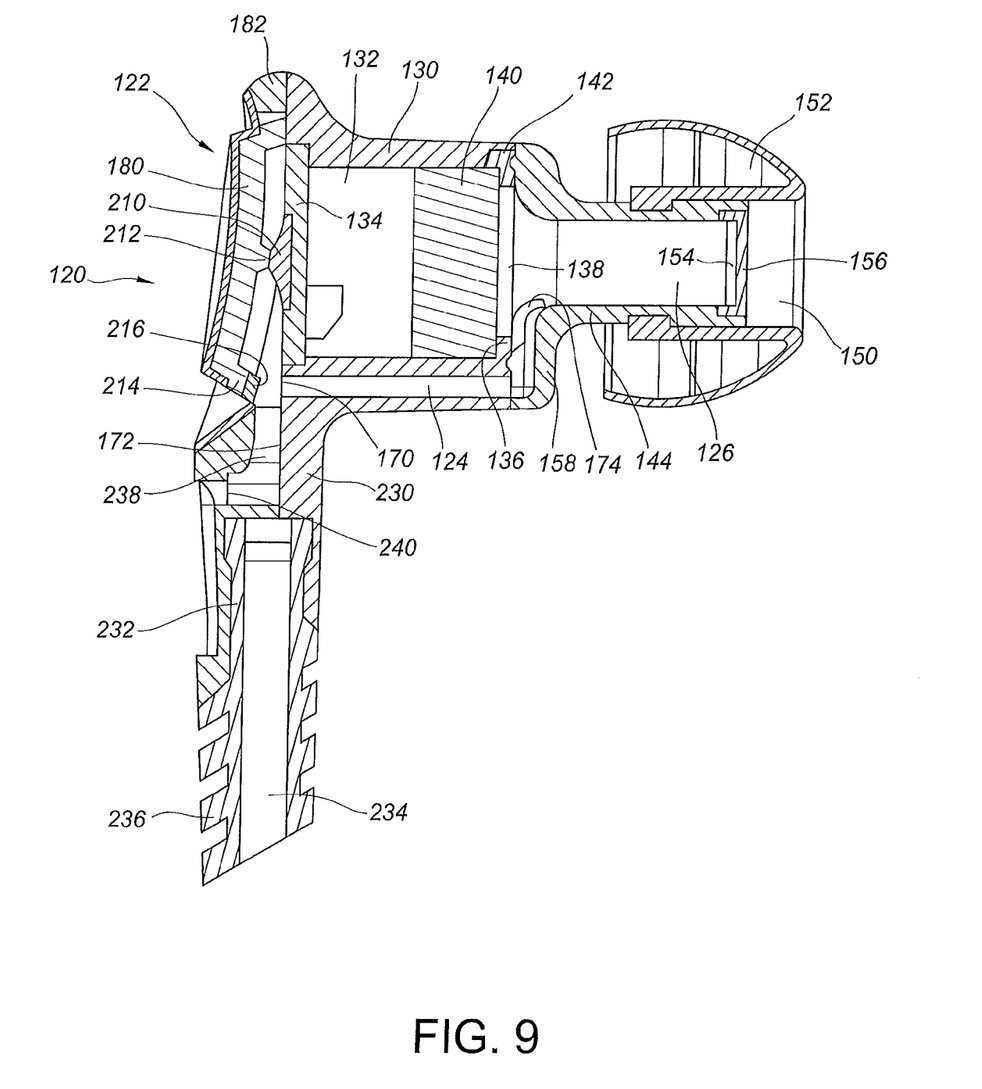
FIG. 9 is a more detailed cross-sectional view of a canal phone incorporating the first embodiment of the invention and showing the hinge mechanism in its open position, in accordance with the present invention.
Figure 10:
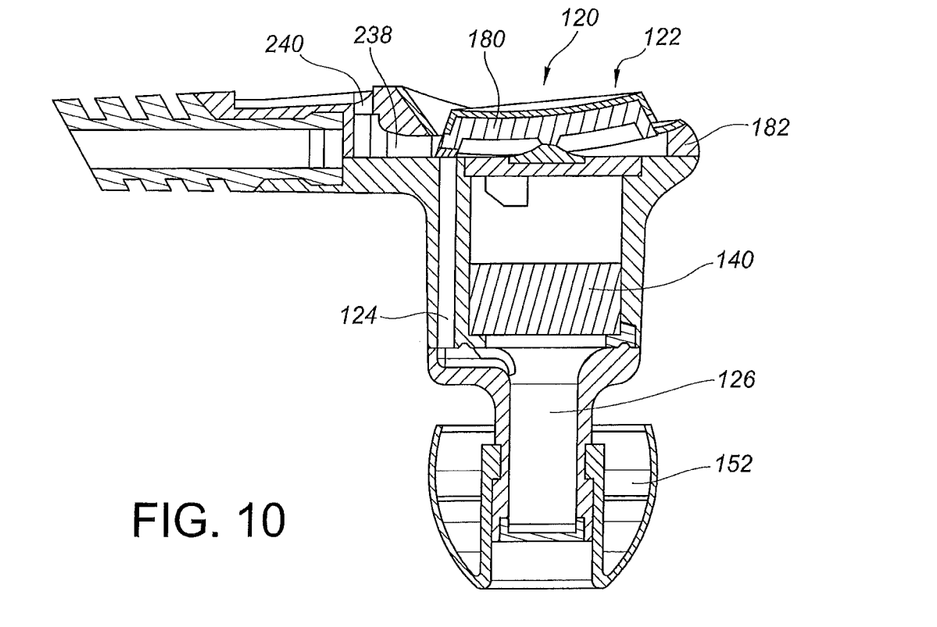
FIG. 10 is a view of the canal phone of FIG. 9, showing the hinge mechanism in its closed position, in accordance with the present invention.
Figure 11:
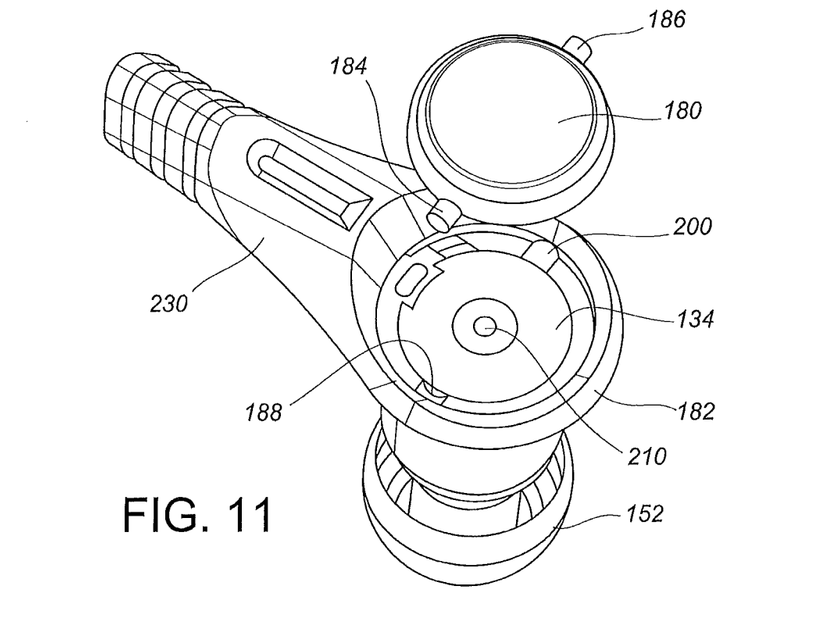
FIG. 11 is a top perspective exploded view of the canal phone of FIG. 9, in accordance with the present invention.

FIGS. 9-11 illustrate in greater detail at 120 a preferred embodiment of the apparatus of the present invention, utilizing a hinged switch 122 that is similar to the hinged switch diagrammatically illustrated by the canal phone of FIGS. 7A and 7B. Switch 122 is mounted so as to selectively open or close an ambient sound passageway 124 which extends from the exterior of the canal phone to an inner sound chamber 126. FIG. 9 illustrates the switch 122 in its open position, wherein ambient sounds are allowed to enter the chamber 126, while FIG. 10 illustrates the switch in its closed position, which isolates the inner chamber from ambient sounds, corresponding to FIGS. 7B and 7A, respectively. FIG. 11 is a perspective view of the canal phone 120 with the switch removed for clearer illustration.

Canal phone 120 is similar to assembly 50, and includes a generally cylindrical external wall 130 surrounding an outer, or rearward chamber 132 having a rear wall 134 and a front wall 136 which serve to form a rear portion of a speaker enclosure. Mounted over an opening 138 in the wall 136 and located in chamber 132 is a dynamic driver, or transducer 140. Secured to the forward end 142 of the wall chamber is a generally cylindrical front wall 144 which surrounds the front, or inner chamber 126 in front of the transducer 140. The forward end of wall 144 engages an inner opening 150 that passes through an ear tip 152, with the end of the wall forming an aperture, or audio port 154 for allowing sounds produced by the transducer to pass into the inner ear of the user. Aperture 154 may be covered by a screen 156, if desired.

The housing portion 144 which defines front sound chamber 126 projects inwardly from the rear enclosure or chamber portion 132, as illustrated, and carries the ear tip or acoustic coupling device 152, as discussed with respect to previous illustrations. As discussed, device 152, which is configured and selected to be inserted into the entrance of an ear canal of a user, is in the form of an ear-tip of a soft compliant material The housing portion 144 has at least one inwardly projecting flange portion 158 which is preferably of generally conical form and of progressively inwardly decreasing diameter, arranged to conform to the inner surface portions of the entrance of the ear canal of the user and to cooperate with the soft tip 152 to provide an acoustic seal limiting transmission of ambient sound to the ear canal.

The hollow elongated passageway 124 may extend through the wall of the outer housing portion 130 along, but separated from, the rear chamber 132, with an open rearward end port, or external port 170 terminating at the rearmost surface 172 of wall 134 separating the rear chamber 132 from the ambient environment outside the assembly 120 and, when in use, outside the user's ear. The passageway 124 terminates at its inner end at an inner port 174 that is in communication with the front chamber 126 by way of a continuation of passageway 124 in wall 144. When passageway 124 is open, it places chamber 126 in audio communication with the ambient environment by way of the outer and inner port 170 and 174. Port or passageway 124 is an acoustical transmission structure preferably sized to enhance the intelligibility of speech and other important ambient sounds, when switch 122 is open and in the illustrated embodiment has an end to end length of 14.2 millimeters and a cross sectional area of 3.23 squared millimeters.

The outer end wall 134 carries a selectively actuable switch, shut-off point, or sealing member 122 configured to permit a user to occlude and substantially seal off the outer aperture 170 defined in the outer end wall to sonically isolate the inner chamber 126 or to uncover the outer aperture 170 so that sound from the ambient environment can pass into and through the outer aperture, through passageway 124, through port 174 and into the inner sound chamber to co-mingle with sound generated by the transducer so that a comingled sound passes through sound port 154 into the user's ear. Two-state user controllable stopper switch mechanism or sound switch 122 thus allows a user to select between (a) a first, sealed state where ambient sound passageway 124 is closed, thus acoustically isolating the listener for enhanced listening performance and (b) a second, open state wherein ambient sound passageway 84 is in open fluid or audio communication with the outside atmosphere and the user can more easily perceive ambient sounds from his or her surrounding environment.

As illustrated in FIGS. 9-11, the switch 122 consists of a pivotable cover 180 shaped to fit within an annular top bracket 182 that is mounted on the top surface 172 of the speaker enclosure wall 130 to form an upstanding flange around the top wall 134. The bracket is shaped to fit the shape of the canal phone 120, which in the illustrated embodiment is generally circular as best illustrated in FIG. 11, and the cover 180, which is shaped to fit within the flange formed by the bracket, is also generally circular. The cover is mounted for pivotal motion by a pair of diametrically opposed pivot pins 184 and 186 that engage corresponding mounting slots 188 and 200 in the bracket 182. A detent and spring assembly 210 is centrally mounted on the top wall 134 to engage a corresponding detent 212 on the bottom of the cover 180 so that when the cover is pivoted about pins 184 and 186, the spring detent will cause the cover to snap between "open" and "closed" positions as illustrated in FIGS. 9 and 10, respectively. The cover 180 incorporates a circumferential downwardly extending shoulder, or flange 214 that carries a sealing pad 216 located to be engageable with the port 170 when the cover is pivoted to the closed position.

The top bracket 182 preferably includes an extension 230 which is configured to receive and secure a wire connector or fitting 232 which incorporates a wire channel 234 for receiving suitable wires for connecting the transducer 140 to a suitable external sound source. The connector incorporates a conventional strain relief section 236 to protect the wires. Extending through the bracket extension 230 is a passageway 238 which provides sonic communication between the port 170 and an aperture 240 in the bracket surface to provide an exit point for the passageway 124 to the ambient environment. Preferably, the exit aperture is configured as an elongated trough or groove optionally covered with a protective screen structure, as seen in FIGS. 10 and 11.

It will be understood that the passageway 124 can be opened to the ambient environment through port 240, and can be closed, by pivoting the switch mechanism 122 between the positions illustrated in FIGS. 9 and 10, as by pressing down (inwardly) on the cover 180 on one or the other sides of the pivot pins 184 and 186. The spring detent 210 causes the cover to snap between the positions and to secure the cover in the selected position until it is again operated. When snapped to the closed position, the port 170 is sealed and, when the canal phone is inserted in a user's ear canal and sealed by the soft tip 152, the inner volume 126 is acoustically isolated from the ambient environment to allow high quality sound to be heard from the transducer 140. When the user desires to hear ambient sounds, it is not necessary to remove the canal phone from the ear; it is only necessary to engage the switch mechanism 122 to open port 170, allowing acoustic communication between the inner chamber 126 and the ambient by way of linked passageway 124, port 170, passageway 238, and exit port 240.

Figure 12:
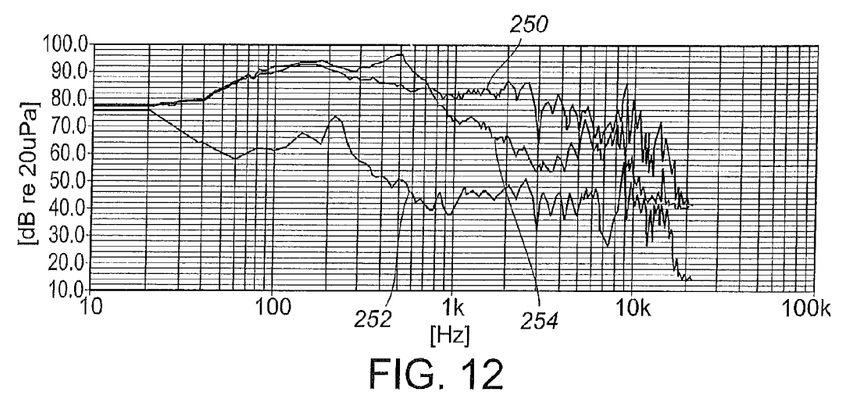
FIG. 12 is a graphical illustration of sound level measurements taken from a mock-up version of the canal phone of FIGS. 9 and 10, in accordance with the present invention.

The acoustic isolation afforded by the canal phone of the present invention is illustrated in FIG. 12, wherein curve 250 illustrates a measurement of background, or ambient noise from the user's surrounding environment. The attenuation or isolation provided by a prototype of the present invention, measured with the ambient sound passageway closed is on the order of −20 dB or more and is broadband in frequency from about 50 Hz to well beyond 20 Hz, as illustrated by curve 252. This isolation is comparable to that provided by some types of isolation earplugs. Opening the ambient sound passageway allows ambient sound to enter the inner chamber of the canal phone at levels indicated by curve 254. As noted above, the port or passageway (e.g., 84 or 124) is an acoustical transmission structure preferably sized to enhance the intelligibility of speech and other important ambient sounds, and when the switch (e.g., 90 or 122) is open, as illustrated, in this case ambient sound in the 50-1 kHz band is present in the inner chamber at near normal levels, while sound levels in the 1 kHz-3 kHz band are reduced in the inner chamber by only 10-15 dB below normal.

Figure 13:
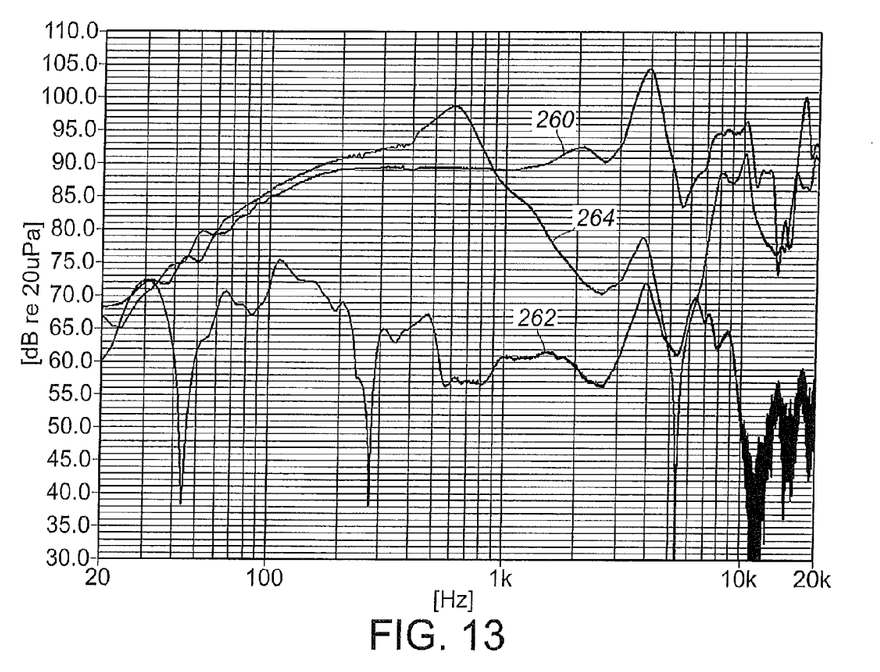
FIG. 13 is a graphical illustration of measurements of ambient sound level, vs. sound level through an isolating earplug, vs. sound level through an open 0.25 mm diameter tube, in accordance with the present invention.

For comparison, FIG. 13 illustrates measurements of ambient sound vs. a standard sound isolating earplug, vs. the same earplug with an open 2.5 mm diameter tube, using a GRAS Ear and Cheek simulator. Measurements were corrected for a diffuse field. Supra aural headphones were used as the ambient noise source. The upper line 260 is a measurement of sound level in an ear canal simulator from the source with no blockage, while the line 262 is a measurement of the source with a foam earplug blocking the ear canal simulator. Line 264 shows a measurement of the source sound level with a similar ear plug in place, but with a 2.5 mm tube through the center as an intentional sound leakage path, simulating the audio passageway illustrated and described above.

Canal phones are typically made by molding the structural and enclosure parts using various plastics, or alternatively machining some of the structural parts from wood, metal or other materials. In the former case, the design of the passageway 124 of FIGS. 9-11 for conducting ambient sound into the molded housing and making the mechanism for opening or closing the passageway by means of an attached moving part—either pivoted, hinged or sliding as described above—is straightforward. A nearly identical result can be achieved by machining the housing/enclosure and attached moving parts, although at a cost premium.

Although pivoted, sliding or hinged switch mechanisms are described herein as examples of the present invention, it will be understood that the selected allowance of, or isolation from, environmental sounds can be achieved by opening or closing the passageway at either end with an additional separate part or cover or by pinching-off or otherwise blocking the passageway at any point along its length. It is also possible to modify the acoustic performance of the canal phone to some desired optimum, as by acoustically tuning the passageway for the open or closed operational modes so that it is optimized for ambient sound passage or sonic performance. Generally, the closed mode is best for sonic performance optimization, given that there are fewer external distractions, and the open mode is best for the passage of ambient environmental sound, for obvious reasons. It will be understood that any of the commonly available transducers used in headphones, canal phones, and ear buds, using balanced armature, dynamic driver or other transducers could be used in these designs.

Figure 14:
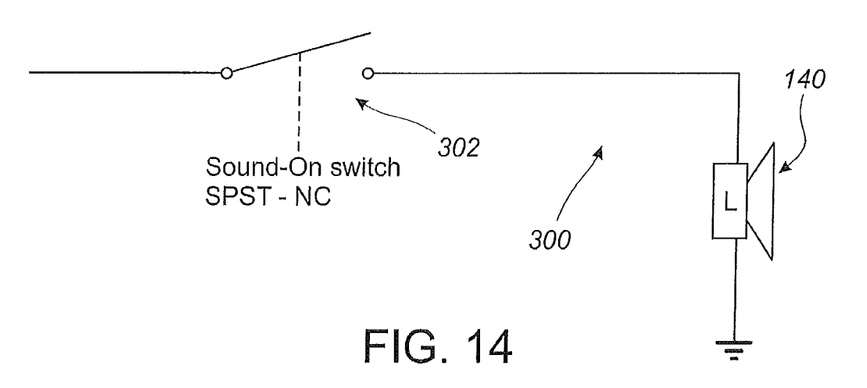
FIG. 14 is a schematic graphical illustration of another embodiment of the canal phone of the present invention, with electrical disconnection of only one earphone speaker in a pair; the Sound-On SPST-NC switch is located in only the left (or alternatively the right) earphone. Actuating the SPST-NC switch both opens the Sound-On port and disconnects the electrical connection to the loudspeaker in the selected (i.e., left or right) earphone, in accordance with the present invention.
Figure 15:
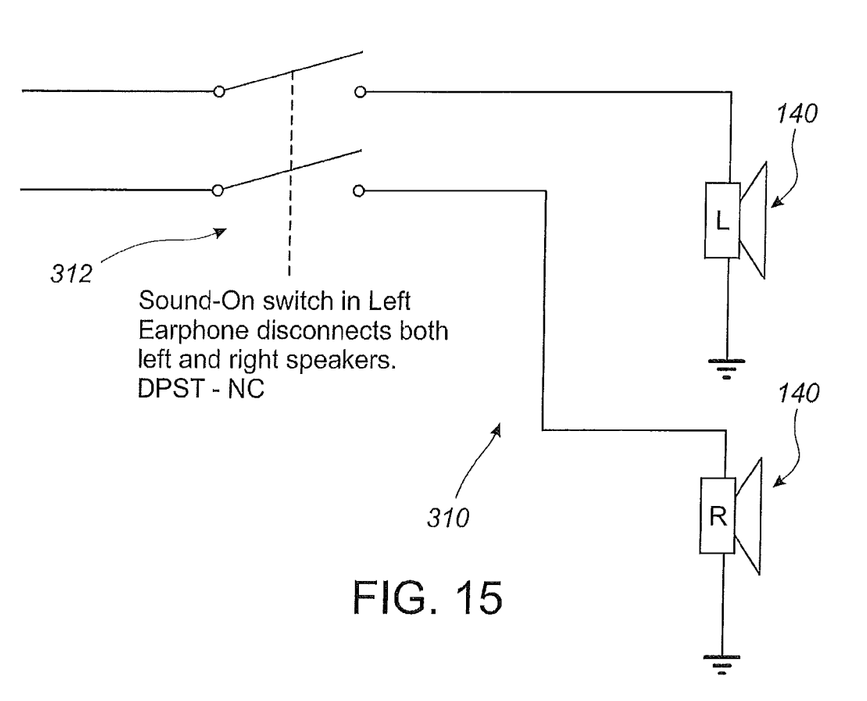
FIG. 15 is a schematic graphical illustration of another embodiment of the canal phone of the present invention, with electrical disconnection of both earphone speakers—The Sound-On DPST-NC switch is located in only the left (or alternatively the right) earphone. Actuating the DPST-NC switch opens the Sound-On port in the left earphone and simultaneously disconnects the electrical connection to the loudspeakers in both the left and right earphones, in accordance with the present invention.

FIGS. 14 and 15 illustrate alternative embodiments of the structure and method of the present invention, the Sound-On port feature is modified or optionally removed. When the Sound-On port switch (e.g., 100, 122 or 240) is opened, the acoustic tuning changes. The acoustic impedance in front of the speaker diaphragm (between the diaphragm and the tympanum) will be reduced significantly, resulting in a loss of low frequency reproduction. It might be possible to tune the earphone such that the bass performance is optimized while the Sound-On port is opened but that would mean that low frequencies would be grossly over-emphasized when the port is closed. It is possible to counteract this tuning difference by including a small crossover network circuit in each earphone that is capable of reducing the bass output back to normal levels when the port is closed. In this case, the Sound-On switch (e.g., 100, 122 or 240) is configured to short or bypass this crossover network so that the tuning can be neutral in both the port open/port closed switch positions.

The embodiment of FIGS. 14 and 15 provides the user with a selectable option to hear the sound source signal and the ambient sound simultaneously and the result in that case will be mingled sounds—much like ear-bud type earphones. Certainly the listener would potentially hear ambient sound but only in competition with the sound source signal level at any moment. A listener could choose to set the switches before beginning some activity during which he or she preferred to hear more ambient sound as well as music, for example, and left in that mode until finished with that activity. This option differs from use of the Sound-On feature to enable them to hear more detailed environmental sound like announcements, or to speak normally with others, etc. while momentarily activating the Sound-On feature. In this case the acoustic performance of the earphone is preferably optimized with the Sound-On port closed and the earphone loudspeaker will not function while the Sound-On port is open (as illustrated in FIGS. 14 and 15). It is possible to configure a primary Sound-On switch so that is disconnects the speakers in both earphones (as illustrated in FIG. 15) although opening the Sound-On port in only one earphone, and this would further enhance the listeners ability to hear conversation normally.

With this in mind, as illustrated in FIGS. 14 and 15, another embodiment of the Sound-On feature is configured to must include the ability of a primary switch in one earphone to break the electrical connection to the speakers in one or both of the earphones while coincidentally opening the Sound-On port in the primary earphone. See the attached simple electrical schematic for one or both. In accordance with the present invention, the Sound-On switch (e.g., 100, 122 or 240) opening or closing the Sound-On port and simultaneously disconnecting or connecting a passive filter (not shown) in the electrical circuit of the earphone is configured to reduce bass output when circuit is connected and the Sound-On port is closed. This method of use involves one switch (e.g., 100, 122 or 240) in each earphone as before, providing electrical disconnection of the earphone speakers by the SoundOn switch.

As noted above, FIG. 14 is a schematic graphical illustration of another embodiment of the canal phone 300 of the present invention, with electrical disconnection of only one earphone transducer (e.g., 140) in a pair; the Sound-On Single Pole Single Throw Normally Closed ("SPST-NC") switch 312 is located in only the left (or alternatively the right) earphone housing. Actuating SPST-NC switch 312 both opens the Sound-On port (e.g., 100, 122 or 240) and disconnects the electrical connection to the loudspeaker or transducer 140 in the selected (i.e., left or right) earphone, in accordance with the present invention.

Turning now to FIG. 15, another embodiment of the canal phone of the present invention 310 provides electrical disconnection of both earphone speakers in a stereo or binaural pair. The Sound-On Double Pole Single Throw Normally Closed ("DPST-NC") switch 312 is preferably located in only the left (or alternatively the right) earphone housing. Actuating DPST-NC switch 312 opens the Sound-On port (e.g., 100, 122 or 240) in the left earphone and simultaneously disconnects the electrical connection to the loudspeaker transducers 140 in both the left and right earphone housings, in accordance with the present invention.

Persons having skill in the art will appreciate that the present invention is well suited in many configurations to provide a canal phone assembly (e.g., 120) having a housing adapted to fill and engage the ear canal 16 of a user, comprising: a housing body having an outer housing portion and an inner housing portion dimensioned to fit within a user's ear canal; a sound chamber within said housing isolated from ambient noise and having a transducer (e.g., 58 or 140) for producing sound in said sound chamber; an ambient sound-transmission passageway for acoustically connecting the sound chamber to a surrounding environment including ambient noise; a finger-actuable switch mechanism on said housing body's outer housing portion for selectively opening and closing said ambient sound-transmission passageway; an inner opening for directing sound from said transducer in said sound chamber to an ear canal of a user, wherein said ambient sound-transmission passageway, when open, is configured for transmitting ambient noise into the sound chamber and to the ear canal of a user, and wherein said switch mechanism is operable to selectively close said passageway to prevent the ambient noise from entering said ear canal through said sound chamber. The canal phone assembly switch mechanism is selectively movable between open and closed positions by a user with a single finger to respectively open or block the ambient sound-transmission passageway, and the ambient sound-transmission passageway has inner and outer ports, the outer port being oriented towards an ambient noise environment outside of the canal phone and a user's ear and the inner port being oriented toward said sound chamber; wherein the sound chamber is formed by a space between said transducer within the canal phone and the user's ear canal; and wherein said switch mechanism is located to open and close said outer port. The canal phone assembly switch mechanism may include a cover pivotally secured to said housing and having a sealing portion movable toward and away from said outer port to close and open it, respectively; and a spring detent for holding the cover in its selected position.

The canal phone assembly may be part of a kit (not shown) which preferably include a pair of canal phone assemblies and plurality of substantially conical or mushroom-head shaped cushioned, resilient ear tips in varying sizes (e.g., like 68) removably disposed over the inner housing portion for engaging and sealing with the ear canal of the user. As noted above, the ambient sound-transmission passageway is an acoustical transmission structure tuned to enhance the intelligibility of speech and other important ambient sounds, when the switch is open, and, depending on housing body configuration can have an end to end length of between 5 and 20 millimeters and a cross sectional area of between 1 and 5 squared millimeters. The ambient sound-transmission passageway terminates in and defines an outer port opening or port exit with a cross sectional area of between 1 and 5 squared millimeters, depending on housing body configuration, and preferably defines an outer port opening or port exit in fluid communication with an elongated screen covered groove or trough shaped depression defined in an exterior wall of the outer housing portion.

The commercial possibilities for the structure and method of the present invention apply chiefly to insertable earphones that are meant to form an acoustic seal in the listener's ear canal, but the features and structural elements of the present invention can be adapted for use in over-ear or circumaural headphones. In this case the passageway that is opened or alternatively closed would still have one end position to optimize the acceptance of the ambient environmental sound and the other positioned in the space between the loudspeaker diaphragm and the listeners tympanum. For circumaural headphones (as opposed to canal phones), this second opening could be outside of the listener's ear canal. The invention could further be extended to circumaural headphones that are used only for noise-reduction in the same manner. The second opening of the passageway allowing the ambient noise to enter could be in the same position as that just stated excepting that in some cases noise reducing headphones do not have loudspeakers, and hence no loudspeaker diaphragm. The enclosed space within the headphones is essentially the same however.

Having described preferred embodiments of a new and improved method, it is believed that other modifications, variations and changes will be suggested to those skilled in the art in view of the teachings set forth herein. It is therefore to be understood that all such variations, modifications and changes are believed to fall within the scope of the present invention.

What is claimed is:

1. A canal phone having a housing adapted to engage the ear canal of a user, comprising:
   a sound chamber within said housing isolated from ambient noise;
   an ambient sound-transmission passageway for acoustically connecting the sound chamber to the ambient noise; wherein said ambient sound-transmission passageway is an acoustical transmission structure in open fluid communication with the outside atmosphere and is acoustically tuned to enhance the intelligibility of speech and other important ambient sounds in the 50-1 kHz band and the 1 kHz to 3 kHz band; and
   a switch mechanism for selectively opening and closing said ambient sound-transmission passageway.

2. The canal phone of claim 1, further including:
   a transducer for producing sound in said sound chamber; and
   an inner opening for directing sound from said transducer in said sound chamber to an ear canal of a user,
   wherein said passageway, when open, is configured for transmitting ambient noise into the sound chamber and to the ear canal of a user, and
   wherein said switch mechanism is operable to selectively close said passageway to prevent ambient noise from entering said ear canal through said sound chamber.

3. The canal phone of claim 2, wherein said switch mechanism is selectively movable between open and closed positions to respectively open or block said passageway.

4. The canal phone of claim 3, wherein said passageway has inner and outer ports, the outer port being oriented towards an ambient noise environment outside of the canal phone and a user's ear and the inner port being oriented toward said sound chamber;
   wherein the sound chamber is formed by a space between said transducer within the canal phone and the user's ear canal; and
   wherein said switch mechanism is located to open and close said outer port.

5. The canal phone of claim 4, wherein said switch mechanism includes:
   a cover pivotally secured to said housing and having a sealing portion movable toward and away from said outer port to close and open it, respectively; and
   a spring detent for holding the cover in its selected position.

6. An acoustic ear piece for use in listening to sound from a selected source, comprising:
   an elongated, tubular housing having an outer end wall and an inner open end disposed opposite the end wall, the housing having an outer enclosure with a volume configured to receive and support a transducer and an inner sound chamber terminating in said inner open end, so that sound generated by the transducer propagates into and through the front sound chamber and out through the inner open end;
   a connector on said housing for receiving electrical conductors extending from an audio signal source external to the housing to the transducer for converting electrical energy received via the conductors to sound energy which is directed into the front sound chamber;
   an elongated passageway having an open inner end terminating in the front sound chamber and an open outer end terminating at an outer port defined in the outer end wall of the housing; wherein said elongated passageway is an acoustical transmission structure in open fluid communication with the outside atmosphere and is acoustically tuned to enhance the intelligibility of speech and other important ambient sounds in the 50-1 kHz band and the 1 kHz to 3 kHz band; and
   a selectively actuable stopper switch mechanism configured to permit a user selectively to plug, block, occlude or cover and seal off the outer aperture defined in the outer end wall, or to uncover the outer aperture defined in the outer end wall so that sound from an ambient environment in communication with said outer aperture can pass into and through the outer aperture defined in the outer end wall and propagate into the front sound chamber, to co-mingle with sound generated by the transducer.

7. The acoustic ear piece of claim 6, further including an ear tip removably disposed over said inner end of said housing for engaging and sealing with an ear canal of a user.

8. The acoustic ear piece of claim 7, wherein said tip is formed from a resilient material.

9. The ear piece of claim 7, wherein said switch mechanism includes:
   a cover pivotally secured to said housing and having a sealing portion movable toward and away from said outer port to close and open it, respectively; and
   a spring detent for holding the cover in its selected position.

10. A canal phone assembly having a housing adapted to fill and engage the ear canal of a user, comprising:
    (a) a housing body having an outer housing portion and an inner housing portion dimensioned to fit within a user's ear canal;

(b) a sound chamber within said housing isolated from ambient noise and having a transducer for producing sound in said sound chamber;

(c) an ambient sound-transmission passageway for acoustically connecting the sound chamber to a surrounding environment including ambient noise;

(d) a finger-actuable switch mechanism on said housing body's outer housing portion for selectively opening and closing said ambient sound-transmission passageway;

(e) an inner opening for directing sound from said transducer in said sound chamber to an ear canal of a user, wherein said ambient sound-transmission passageway, when open, is configured for transmitting ambient noise into the sound chamber and to the ear canal of a user;

wherein said ambient sound-transmission passageway is an acoustical transmission structure in open fluid communication with the outside atmosphere and is acoustically tuned to enhance the intelligibility of speech and other important ambient sounds in the 50-1 kHz band and the 1 kHz to 3 kHz band; and wherein said switch mechanism is operable to selectively close said passageway to prevent the ambient noise from entering said ear canal through said sound chamber.

11. The canal phone assembly of claim 10, wherein said switch mechanism is selectively movable between open and closed positions by a user with a single finger to respectively open or block said ambient sound-transmission passageway.

12. The canal phone assembly of claim 11, wherein said ambient sound-transmission passageway has inner and outer ports, the outer port being oriented towards an ambient noise environment outside of the canal phone and a user's ear and the inner port being oriented toward said sound chamber;

wherein the sound chamber is formed by a space between said transducer within the canal phone and the user's ear canal; and wherein said switch mechanism is located to open and close said outer port.

13. The canal phone assembly of claim 12, wherein said switch mechanism includes:

a cover pivotally secured to said housing and having a sealing portion movable toward and away from said outer port to close and open it, respectively; and a spring detent for holding the cover in its selected position.

14. The canal phone assembly of claim 13, further including an ear tip removably disposed over an inner housing portion for engaging and sealing with the ear canal of the user.

15. The canal phone assembly of claim 13, further including an electrical switch connected in series with said transducer and configured to disconnect said transducer when said switch mechanism is in said open position and said ambient sound-transmission passageway is open.

16. The canal phone assembly of claim 15, wherein said ambient sound-transmission passageway is an acoustical transmission structure tuned to enhance the intelligibility of speech and other important ambient sounds, when said switch is open.

17. The canal phone assembly of claim 16, wherein said ambient sound-transmission passageway is an acoustical transmission structure has an end to end length of between 5 and 20 millimeters and a cross sectional area of between 1 and 5 squared millimeters.

18. The canal phone assembly of claim 17, wherein said ambient sound-transmission passageway is an acoustical transmission structure has an end to end length of 14.2 millimeters and a cross sectional area of 3.23 squared millimeters.

19. The canal phone assembly of claim 16, wherein said ambient sound-transmission passageway defines an outer port opening or port exit with a cross sectional area of between 1 and 5 squared millimeters.

20. The canal phone assembly of claim 16, wherein said ambient sound-transmission passageway defines an outer port opening or port exit in fluid communication with an elongated groove or trough shaped depression defined in an exterior wall of said outer housing portion.

21. A canal phone assembly having a housing adapted to fill and engage the ear canal of a user, comprising:

(a) a housing body having an outer housing portion and an inner housing portion dimensioned to fit within a user's ear canal;

(b) a sound chamber within said housing isolated from ambient noise and having a transducer for producing sound in said sound chamber;

(c) an ambient sound-transmission passageway for acoustically connecting the sound chamber to a surrounding environment including ambient noise;

(d) a finger-actuable switch mechanism on said housing body's outer housing portion for selectively opening and closing said ambient sound-transmission passageway;

(e) an inner opening for directing sound from said transducer in said sound chamber to an ear canal of a user, wherein said ambient sound-transmission passageway, when open, is configured for transmitting ambient noise into the sound chamber and to the ear canal of a user, and wherein said switch mechanism is operable to selectively close said passageway to prevent the ambient noise from entering said ear canal through said sound chamber;

wherein said switch mechanism is selectively movable between open and closed positions by a user with a single finger to respectively open or block said ambient sound-transmission passageway;

wherein said ambient sound-transmission passageway has inner and outer ports, the outer port being oriented towards an ambient noise environment outside of the canal phone and a user's ear and the inner port being oriented toward said sound chamber;

wherein the sound chamber is formed by a space between said transducer within the canal phone and the user's ear canal;

wherein said switch mechanism is located to open and close said outer port;

wherein said switch mechanism includes:

a cover pivotally secured to said housing and having a sealing portion movable toward and away from said outer port to close and open it, respectively;

a spring detent for holding the cover in its selected position;

further including an electrical switch connected in series with said transducer and configured to disconnect said transducer when said switch mechanism is in said open position and said ambient sound-transmission passageway is open;

wherein said ambient sound-transmission passageway is an acoustical transmission structure tuned to enhance the intelligibility of speech and other important ambient sounds, when said switch is open;

wherein said ambient sound-transmission passageway is an acoustical transmission structure has an end to end length of between 5 and 20 millimeters and a cross sectional area of between 1 and 5 squared millimeters; and wherein said ambient sound-transmission passageway is an acoustical transmission structure has an end to end length of 14.2 millimeters and a cross sectional area of 3.23 squared millimeters.

* * * * *